US009282970B2

(12) United States Patent
Lee et al.

(10) Patent No.: US 9,282,970 B2
(45) Date of Patent: Mar. 15, 2016

(54) SYSTEMS AND METHODS FOR POSITIONING AND COMPACTING A BODILY IMPLANT

(71) Applicant: Covidien LP, Mansfield, MA (US)

(72) Inventors: Stephen W. Lee, San Jose, CA (US); Ric C. Leguidleguid, Union City, CA (US); Walter J. Stevens, III, San Jose, CA (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 14/042,653

(22) Filed: Sep. 30, 2013

(65) Prior Publication Data
US 2015/0094752 A1    Apr. 2, 2015

(51) Int. Cl.
*A61F 2/06* (2013.01)
*A61B 17/12* (2006.01)
*A61B 17/00* (2006.01)

(52) U.S. Cl.
CPC ..... *A61B 17/12022* (2013.01); *A61B 17/12031* (2013.01); *A61B 17/12036* (2013.01); *A61B 17/12109* (2013.01); *A61B 17/12172* (2013.01); *A61B 2017/00004* (2013.01); *A61B 2017/1205* (2013.01); *A61B 2017/12054* (2013.01)

(58) Field of Classification Search
CPC ................. A61B 17/12022; A61B 2017/1205; A61B 17/12109; A61B 17/12031; A61B 17/12036; A61B 2017/12054; A61F 2/95; A61F 2002/9505; A61F 2002/9511; A61F 2002/9522; A61F 2002/011
See application file for complete search history.

(56) References Cited

U.S. PATENT DOCUMENTS

| 5,658,308 | A  | * | 8/1997  | Snyder    | A61B 17/12022 606/191  |
|-----------|----|---|---------|-----------|------------------------|
| 6,368,338 | B1 | * | 4/2002  | Konya     | A61B 17/12022 606/200  |
| 7,815,661 | B2 |   | 10/2010 | Mirizzi et al. |                   |
| 7,972,354 | B2 |   | 7/2011  | Prestezog et al. |                 |
| 2001/0044629 | A1 | * | 11/2001 | Stinson | A61B 17/12022 606/108 |
| 2003/0171771 | A1 | * | 9/2003 | Anderson | A61B 17/221 606/200 |
| 2004/0176798 | A1 | * | 9/2004 | Epstein | A61B 17/00491 606/213 |
| 2005/0267528 | A1 |   | 12/2005 | Ginn et al. |                    |

(Continued)

FOREIGN PATENT DOCUMENTS

AU    2013205104 A1    5/2013
CN       1319380 A     10/2001

(Continued)

OTHER PUBLICATIONS

Extended Search Report from counterpart European Patent Application No. 14185985.0, dated Feb. 9, 2015, 10 pp.

(Continued)

*Primary Examiner* — Jonathan W Miles
(74) *Attorney, Agent, or Firm* — Thomas M. Johnston, Esq.

(57) ABSTRACT

Bodily implants that can be compacted in a distal-to-proximal direction, and which facilitate repositioning of the implant after compaction. The implants include at least one pull string for expanding the implant in a radial direction while compacting the implant in the longitudinal direction. Where multiple pull strings are provided, they can be secured to the implant at spaced locations along the implant length, and pulled successively to compact the implant in a distal-to-proximal direction. A guide member may also be provided to receive the pull strings and facilitate longitudinal compaction.

26 Claims, 11 Drawing Sheets

(56) References Cited

U.S. PATENT DOCUMENTS

| | | | |
|---|---|---|---|
| 2006/0116713 A1* | 6/2006 | Sepetka | A61B 17/12022 606/200 |
| 2006/0212127 A1 | 9/2006 | Karabey et al. | |
| 2007/0166345 A1* | 7/2007 | Pavcnik | A61B 17/12022 424/423 |
| 2008/0103585 A1* | 5/2008 | Monstadt | A61B 17/12022 623/1.22 |
| 2010/0160898 A1 | 6/2010 | Mirizzi | |
| 2010/0160946 A1* | 6/2010 | Mirizzi | A61B 17/12022 606/191 |
| 2011/0040366 A1 | 2/2011 | Goetz et al. | |
| 2011/0172697 A1* | 7/2011 | Jonsson | A61B 17/12036 606/194 |
| 2011/0313507 A1 | 12/2011 | Ray et al. | |
| 2012/0065668 A1 | 3/2012 | Ginn et al. | |
| 2012/0330226 A1 | 12/2012 | Lee | |
| 2013/0211495 A1* | 8/2013 | Halden | A61B 17/12022 623/1.12 |

FOREIGN PATENT DOCUMENTS

| | | |
|---|---|---|
| CN | 101155567 A | 4/2008 |
| CN | 101212938 A | 7/2008 |
| CN | 101998845 A | 3/2011 |
| CN | 102300509 A | 12/2011 |
| EP | 1169969 A1 | 1/2002 |
| WO | WO9716219 A1 | 5/1997 |
| WO | 0172240 A1 | 10/2001 |
| WO | 2006078578 A2 | 7/2006 |
| WO | 2006118863 A2 | 11/2006 |
| WO | 2010071856 A1 | 6/2010 |
| WO | WO2012052469 A1 | 4/2012 |

OTHER PUBLICATIONS

First Office Action and Search Report, and translation thereof, from counterpart Chinese Application No. 201410513223.8, dated Dec. 28, 2015, 14 pp.

* cited by examiner

SYSTEMS AND METHODS FOR POSITIONING AND COMPACTING A BODILY IMPLANT

TECHNICAL FIELD

The present embodiments relate to medical treatment devices and procedures, in particular to positioning and compacting a bodily implant.

BACKGROUND

Various treatments are commonly used for treating diseases of hollow anatomical structures (HAS), such as venous reflux disease and other diseases. One example endovenous treatment involves placement of an occluding implant in the HAS, such as in the great saphenous vein (GSV). The implant may be, for example, a bioresorbable fibrous body, which may be textured to impart bulk. The implant causes a partial occlusion of the HAS, followed by a complete or substantially complete occlusion, such as by formation of an organic fibrotic occlusion resulting from the body's natural foreign body healing response.

After placing the implant at the treatment site, the implant may be expanded to partially or fully occlude the HAS in the radial direction. For example, the implant may be self-expanding. Alternatively, or in addition, a system for placing the implant may include a mechanism for manually expanding the implant. However, in some instances, the implant in its radially expanded condition does not occlude the HAS sufficiently to cause a complete or substantially complete occlusion to treat the disease. Such a lack of total occlusion maybe cause by not enough radial expansion and/or not enough density of material.

Further, in some cases, initial placement of the implant may not be as desired. In such cases, it is desirable to reposition the implant one or more times until the desired placement is achieved.

SUMMARY

The present embodiments have several features. Without limiting the scope of the present embodiments as expressed by the claims that follow, their features now will be discussed briefly. After considering this discussion, and particularly after reading the section entitled "Detailed Description," one will understand how the features of the present embodiments provide the advantages described herein.

In general, in one aspect, the implementation of the disclosure features a medical treatment system including an elongate, flexible, tubular pushrod having a distal end. The medical treatment system further includes a guide member coupled adjacent the distal end of the pushrod. The medical treatment system further includes an implant coupled adjacent the distal end of the pushrod and proximal of the guide member and extending proximally along the pushrod. The implant has a proximal portion adjacent a proximal end and a distal portion adjacent a distal end. The implant includes a plurality of bioabsorbable fibers. The medical treatment system further includes a distal pull string extending through the guide member and secured to the implant at a first attachment point within the distal portion of the implant. The medical treatment system further includes a proximal pull string extending through the guide member and secured to the implant at a second attachment point within the proximal portion of the implant. Pulling the distal pull string in a proximal direction compacts at least a portion of the distal portion of the implant in a distal direction, and pulling the proximal pull string in a proximal direction compacts at least a portion of the proximal portion of the implant in a distal direction.

One or more of the following features may be included. The implant may further include an intermediate portion disposed between the distal portion and the proximal portion, and an intermediate pull string extending through the guide member and secured to the implant at a third attachment point within the intermediate portion of the implant, wherein pulling the intermediate pull string in a proximal direction compacts at least a portion of the intermediate portion of the implant in a distal direction.

The guide member may be bioabsorbable. The guide member may be tubular and U-shaped.

The medical treatment system may further include an elongate, flexible wire extending through the pushrod. The pushrod may include a first opening and a second opening adjacent the distal end of the pushrod. The first and second openings in the pushrod may be spaced from one another axially along a length of the pushrod. The wire may extend out of the pushrod through the first opening and extend back into the pushrod through the second opening. The guide member may extend through a space bounded by the pushrod and the wire and located between the first and second openings in the pushrod. The guide member may include at least first and second internal passages extending therethrough. Alternatively, the implant may extend through a space bounded by the pushrod and the wire and located between the first and second openings in the pushrod.

In general, in another aspect, the implementation of the disclosure features a medical treatment system including an elongate, flexible pushrod having a distal end. The medical treatment system includes an implant coupled adjacent the distal end of the pushrod and extending proximally along the pushrod. The implant has a proximal portion adjacent a proximal end and a distal portion adjacent a distal end. The implant includes a plurality of bioabsorbable fibers. The medical treatment system further includes a distal pull string secured to the implant at a first attachment point within the distal portion of the implant. The distal pull string extends distally along the pushrod from the first attachment point and then proximally along the implant. The medical treatment system further includes a proximal pull string secured to the implant at a second attachment point within the proximal portion of the implant. The proximal pull string extends distally along the pushrod from the second attachment point and then proximally along the implant.

One or more of the following features may be included. The pushrod may be a hypotube. A side wall of the distal end of the pushrod may include a spiral-shaped cut.

The medical treatment system may further include a guide member coupled adjacent the distal end of the pushrod and distal to the distal end of the implant. The pull strings may extend through the guide member. The guide member may be bioabsorbable. The guide member may be tubular and U-shaped.

The medical treatment system may further include an elongate, flexible wire extending through the pushrod. The pushrod may include a first opening and a second opening adjacent the distal end of the pushrod. The first and second openings in the pushrod may be spaced from one another axially along a length of the pushrod. The wire may extend out of the pushrod through the first opening and extend back into the pushrod through the second opening.

The medical treatment system may further include a guide member, wherein the guide member extends through a space bounded by the pushrod and the wire and located between the first and second openings in the pushrod. The guide member may include first and second internal passages extending therethrough. Alternatively, the distal pull string and the proximal pull string may extend through a space bounded by the pushrod and the wire and located between the first and second openings in the pushrod.

In general, in another aspect, the implementation of the disclosure features an implant for occluding a hollow anatomical structure (HAS). The implant includes a body portion having a proximal portion adjacent to a proximal end, a distal portion adjacent to a distal end, and an intermediate portion disposed between the proximal and distal portions. The body portion includes a plurality of bioabsorbable fibers. The implant further includes a distal pull string secured to the implant at a first attachment point within the distal portion of the implant. The implant further includes a proximal pull string secured to the implant at a second attachment point within the proximal portion of the implant. The implant further includes an intermediate pull string secured to the implant at a third attachment point within the intermediate portion. The pull strings are configured to extend distally of the body portion and then proximally of the body portion, and are configured to be pulled proximally to sequentially compact the distal portion of the body portion, the intermediate portion of the body portion, and the proximal portion of the body portion in a distal direction.

One or more of the following features may be included. The implant may be in combination with a pushrod, wherein the implant is coupled adjacent a distal end of the pushrod. The combination may further include a guide member coupled adjacent the distal end of the pushrod. The pull strings may extend through the guide member. The guide member may be bioabsorbable. The guide member may be tubular and U-shaped. The combination may further include an elongate, flexible wire extending through the pushrod. The pushrod may include a first opening and a second opening adjacent the distal end of the pushrod. The first and second openings in the pushrod may be spaced from one another axially along a length of the pushrod. The wire may extend out of the pushrod through the first opening and extends back into the pushrod through the second opening. The guide member may extend through a space bounded by the pushrod and the wire and located between the first and second openings in the pushrod. Alternatively, the distal, proximal and intermediate pull strings may extend through a space bounded by the pushrod and the wire and located between the first and second openings in the pushrod.

In general, in another aspect, the implementation of the disclosure features a method of treating a hollow anatomical structure (HAS). The method includes inserting a bioabsorbable fibrous implant into the HAS. The implant includes a body portion having a proximal portion adjacent a proximal end and a distal portion adjacent a distal end. The implant further includes a distal pull string secured to the implant at a first attachment point within the distal portion of the implant. The implant further includes a proximal pull string secured to the implant at a second attachment point within the proximal portion of the implant. The method further includes pulling the distal pull string proximally to compact at least a portion of the distal portion of the body portion in a distal direction. The method further includes pulling the proximal pull string proximally to compact at least a portion of the proximal portion of the body portion distally.

One or more of the following features may be included. The pull strings may be pulled consecutively, with the distal pull string being pulled first, and the proximal pull string being pulled next. Inserting the implant into the HAS may include pushing the implant with an elongate, flexible pushrod having a distal end, the implant being coupled adjacent the distal end of the pushrod. The pushrod may be tubular. An elongate, flexible wire may extend through the pushrod. The pushrod may include a first opening and a second opening adjacent the distal end of the pushrod. The first and second openings in the pushrod may be spaced from one another axially along a length of the pushrod. The wire may extend out of the pushrod through the first opening and extend back into the pushrod through the second opening. The implant may extend through a space bounded by the pushrod and the wire and located between the first and second openings in the pushrod. Alternatively, the distal and proximal pull strings may extend through a space bounded by the pushrod and the wire. The method may further include pulling the wire proximally with respect to the pushrod to disengage the implant from the pushrod.

The body portion may further include an intermediate portion disposed between the distal portion and the proximal portion. The implant may further include an intermediate pull string secured to the implant at a third attachment point within the intermediate portion of the implant. The method may further include pulling the intermediate string proximally to compact at least a portion of the intermediate portion of the body portion in a distal direction.

In general, in another aspect, the implementation of the disclosure features a method of treating a hollow anatomical structure (HAS). The method includes inserting an elongate, flexible pushrod into the HAS. The pushrod has a guide member coupled adjacent a distal end of the pushrod and a bioabsorbable fibrous implant coupled adjacent a distal end of the pushrod and proximal to the guide member. The implant includes a body portion having a proximal portion adjacent a proximal end, a distal portion adjacent a distal end, and an intermediate portion disposed between the proximal portion and the distal portion. The implant further includes a distal pull string secured to the implant at a first attachment point within the distal portion of the implant and extending distally through the guide member and then proximally along the pushrod. The implant further includes a proximal pull string secured to the implant at a second attachment point within the proximal portion of the implant and extending distally through the guide member and then proximally along the pushrod. The implant further includes an intermediate pull string secured to the implant at a third attachment point within the intermediate portion of the implant and extending distally through the guide member and then proximally along the pushrod. The method further includes pulling the distal pull string proximally to compact at least a portion of the distal portion of the body portion in a distal direction. The method further includes pulling the intermediate pull string proximally to compact at least a portion of the intermediate portion of the body portion in a distal direction. The method further includes pulling the proximal pull string proximally to compact at least a portion of the proximal portion of the body portion in a distal direction.

The present embodiments provide apparatus and methods for positioning and compacting a bodily implant. For example, the implant includes at least a distal pull string for compacting at least a portion of a distal portion of the implant in the distal direction, and a proximal pull string for compacting at least a portion of a proximal portion of the implant in the distal direction. The invention may provide one or more of the following advantages. Compacting the implant in the distal direction provides more implant material in a specific area by increasing the diameter and the density of the implant in that area. Further, because the compaction of the implant tends to cause the implant to expand further radially than it might naturally, the implant may start with a smaller diameter initially, thereby requiring a smaller insertion sheath. For example, an insertion sheath of 8F may be reduced to 6F, which may reduce patient discomfort during the procedure and aide in faster healing. Further still, compacting the implant in the distal-to-proximal direction (i.e., distal portion first, then proximal portion) facilitates reversing the compaction operation so that the implant can be repositioned within the body in the event that the initial placement is not as desired.

BRIEF DESCRIPTION OF THE DRAWINGS

The present embodiments now will be discussed in detail with an emphasis on highlighting the advantageous features. These embodiments are for illustrative purposes only. These drawings include the following figures, in which like numerals indicate like parts.

DETAILED DESCRIPTION

Figure 1A:
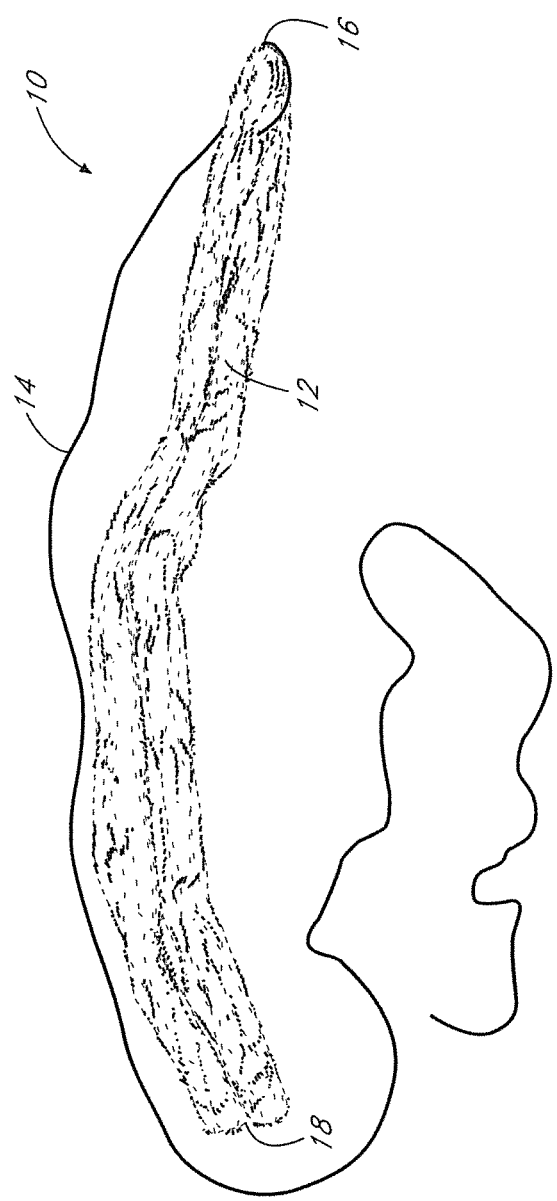
FIG. 1A is a side elevation view of a fibrous bodily implant.

The following detailed description describes the present embodiments with reference to the drawings. In the drawings, reference numbers label elements of the present embodiments. These reference numbers are reproduced below in connection with the discussion of the corresponding drawing features.

Directional terms used herein, such as proximal, distal, upper, lower, clockwise, counterclockwise, etc., are used with reference to the configurations shown in the figures. For example, a component that is described as rotating clockwise when viewed from the perspectives shown in the figures may be said to rotate counterclockwise when viewed from the opposite perspective. Furthermore, the present embodiments may be modified by altering or reversing the positions or directions of movement of various components. Accordingly, directional terms used herein should not be interpreted as limiting.

FIG. 1A illustrates one example of an implant 10 for occlusion of a hollow anatomical structure (HAS). The implant 10 comprises a bioresorbable body 12. In one embodiment, the body 12 comprises a bioresorbable material in fibrous form, which can comprise a collection of individual fibers that can be spun into multi-filament yarns. The fibers or yarns can be textured to impart bulk. In one embodiment, multiple fibers or yarns can be assembled together to form the body 12. The textured fibers or yarns can be made wavy to prevent adjacent yarns from lying closely together and impart bulk and a self-expanding property to the body 12. The fibers can be treated and/or agglomerated in any suitable manner to achieve a desired texture, density, geometry, etc. The fibers can be made or treated such that the body 12 can be compressible and/or expandable. For example, as shown in the illustrated embodiment, the body 12 can naturally assume a radially expanded condition and convert to a compressed condition upon application of a compressive force. Alternatively, the body 12 can naturally assume a compressed condition and convert to an expanded condition upon application of an expansive force. The bioresorbable material can be any suitable bioresorbable material, such as a material from the family of alpha hydroxy acids, for example polylactide (PLA) and/or polyglycolide (PGA).

Exemplary suitable forms and materials for the bulked fibrous bioresorbable body (and/or individual yarns or fibers) are disclosed in U.S. Patent Application Publication No. 2006/0212127, published Sep. 21, 2006, entitled, "Structures for Permanent Occlusion of a Hollow Anatomical Structure," and U.S. Patent Application Publication No. 2007/0248640, published Oct. 25, 2007, entitled, "Occlusive Implant and Methods for Hollow Anatomical Structure." The entireties of these publications are incorporated herein by reference, in particular paragraphs 10-171 of Publication No. 2007/0248640 and the drawings referenced in those paragraphs.

The implant further includes a tether 14 coupled to the body 12. As one example, the body 12 can be generally elongated with a distal end 16 and a proximal end 18, with the distance between the distal end 16 and the proximal end 18 (the length of the body 12) optionally being greater than the cross-sectional diameter of the body 12. The tether 14 is coupled near or to the distal end 16 of the body 12. Body 12 may be formed by folding the fibers of the body 12 over themselves, wherein the fold forms the distal end 16 and the tether 14 is tied around the fold. The tether 14 can be coupled to the body 12 in any suitable manner, examples of which include tying or stitching the tether 14 to the body 12, employing a coupling agent, such as a bioresorbable or non-bioresorbable adhesive, and making the tether 14 integral with the body 12. The tether 14 can have any suitable length relative to the length of the body 12. For example, the length of the tether 14 can be greater than, equal to, or less than that of the body 12.

The tether 14 can be bioresorbable and made of the same material as the body 12 or of a material different than that of the body 12. Alternatively, the tether 14 can be non-bioresorbable. Further, the tether 14 can be inelastic or elastic. In one embodiment, the tether 14 is made of the same bioresorbable material as the body 12, the body 12 comprises multiple fibers processed and textured such that the body 12 is bulked, elastic, and compressible, and the tether 14 comprises multiple fibers spun into a single, relatively smooth, and inelastic yarn, wherein the cross-sectional diameter of the body 12 in its natural expanded condition is significantly greater than the cross-sectional diameter of the tether 14.

The implant 10 can be positioned in a HAS, such as a vessel, to occlude the HAS such that blood flow through the HAS is reduced or prevented. While the implant 10 can be positioned in the HAS in any suitable manner, such as the manners disclosed in the above-incorporated material from the patent application publications, additional or alternative techniques and/or apparatus can be employed, as discussed herein.

In one exemplary embodiment, the implant body 12 has an overall linear mass density of 7200 denier, and is formed from 48 plies of 75 denier, 30 filament, 100% polyglycolide (PGA) yarns. The PGA material has a molecular weight (Mn) over 12,750 and a polydispersity index (PDT) between 1.1 and 1.8. A 30 cm length of the collected 48 plies has a breaking load between 30 and 50 lbf. Among the 48 plies, 24 are "S" twisted and 24 are "Z" twisted, all with a false twist texture of 90 twists per inch. The yarns are false twisted individually using pin twist texturing. The 48 plies are doubled over once at the distal end 16 of the body 12 to create a 7200 denier implant body 12. The tether 14 is formed from 16 plies of 75 denier, 30 filament, 100% polyglycolide (PGA) yarns. The filament denier is 2.5, or about 2.5. All 16 plies are "Z" twisted between 3 and 4 twists per inch and heat set. A 40 cm length of the collected 16 plies has a breaking load between 10 and 17 lbf.

The bulked yarn can be cut to the appropriate length (preferably 50 cm) and the tether 14 is tied to the midpoint. The two halves of the yarn are folded against each other to form the implant body 12 with the tether 14 tied at the now formed distal end 16 of the body 12.

The above specified parameters for the implant body 12 and tether 14 are exemplary only, and can be varied or disregarded in other embodiments. For example, bioabsorbable materials other than PGA, such as polylactic acid (PLA), or any other suitable bioabsorbable or bioresorbable material specified herein can be employed, either alone or in combination with other such materials. For example, a mixture of PGA and PLA plies/fibers/filaments can be used. Non-bioabsorbable or non-bioresorbable materials can be employed as well. In other embodiments, the filament denier in the body 12 can vary as necessary between 1.5 and 3.5, or, between 0.5 and 5.0, while the filament count can vary between 2000 and 4000, or between 1000 and 5000, or otherwise to fall within the above specified ranges for linear mass density. Where PGA is used in forming the body 12, the molecular weight (Mn) can vary between 10,000 and 15,000, or between 5,000 and 20,000.

Figure 1B:
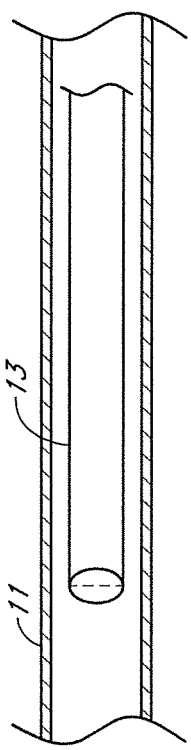
FIGS. 1B-1D are schematic views of a method for delivering a bodily implant into a hollow anatomical structure (HAS)
Figure 1C:
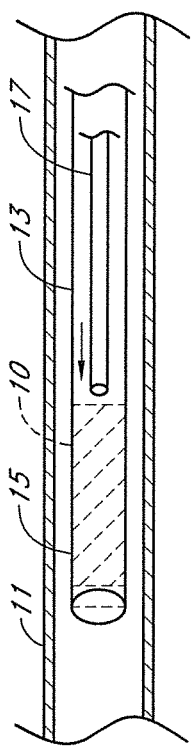
Figure 1D:
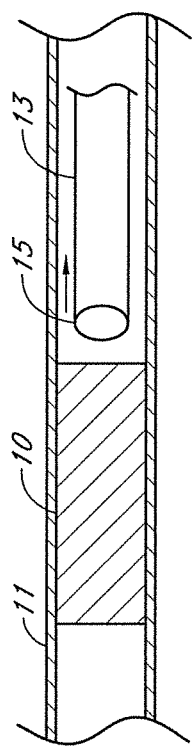

FIGS. 1B-1D illustrate one embodiment of a method of delivering the implant 10 into a hollow anatomical structure (HAS) 11, a delivery catheter 13 and/or sheath is inserted into the HAS 11. The HAS 11 can be a vein, e.g., the greater saphenous vein (GSV), or short saphenous vein (SSV), or other HAS 11, such as, for example, a fallopian tube, ovarian vein, or internal spermatic vein.

The implant 10 is loaded into the delivery catheter 13. The implant 10 may take on a radially compressed configuration when in the delivery catheter 13. The implant 10 is pushed to a distal end portion 15 of the delivery catheter 13. In some embodiments, a pushrod 17 can be used to advance the implant 10. With reference to FIG. 1D, the implant 10 is pushed out of the distal end portion 15 of the delivery catheter 13 and into the HAS 11. In some embodiments, the pushrod 17 can be used to urge the implant 10 distally. In some other embodiments, the pushrod 17 can be held generally stationary and the delivery catheter 13 can be pulled proximally to deliver the implant 10 into the HAS 11. The implant 10 may subsequently be compacted, as described further below, to take on a treatment state or expanded configuration when in place in the HAS 11. The implant 10 preferably forms a scaffold for occlusive ingrowth and clotting in the implant 10, eventually forming a durable occlusion of the HAS 11.

When, for example, treating a saphenous vein such as the GSV, the catheter 13 can be inserted into the HAS 11 at an insertion site remote from the sapheno-femoral junction within the GSV, and advanced toward or to the sapheno-femoral junction. The implant 10 is then advanced through the catheter 13 toward or to the sapheno-femoral junction. If desired, the implant 10 can be placed in the vein such that it extends from the sapheno-femoral junction all the way to the insertion site.

Figure 2A:
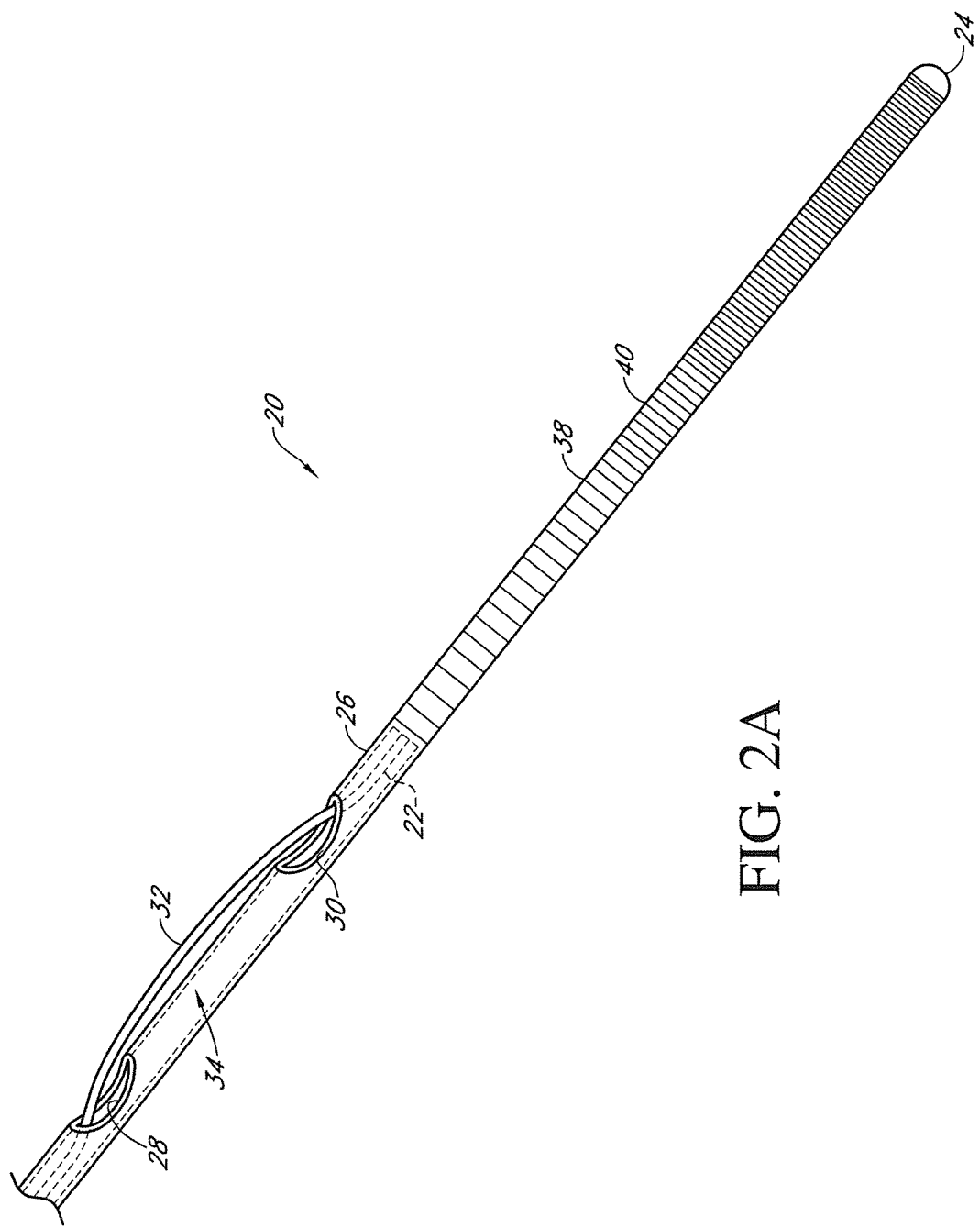
FIGS. 2A and 2B are side elevation views of a pushrod configured for use in a system for placing and compacting a fibrous bodily implant.
Figure 2B:
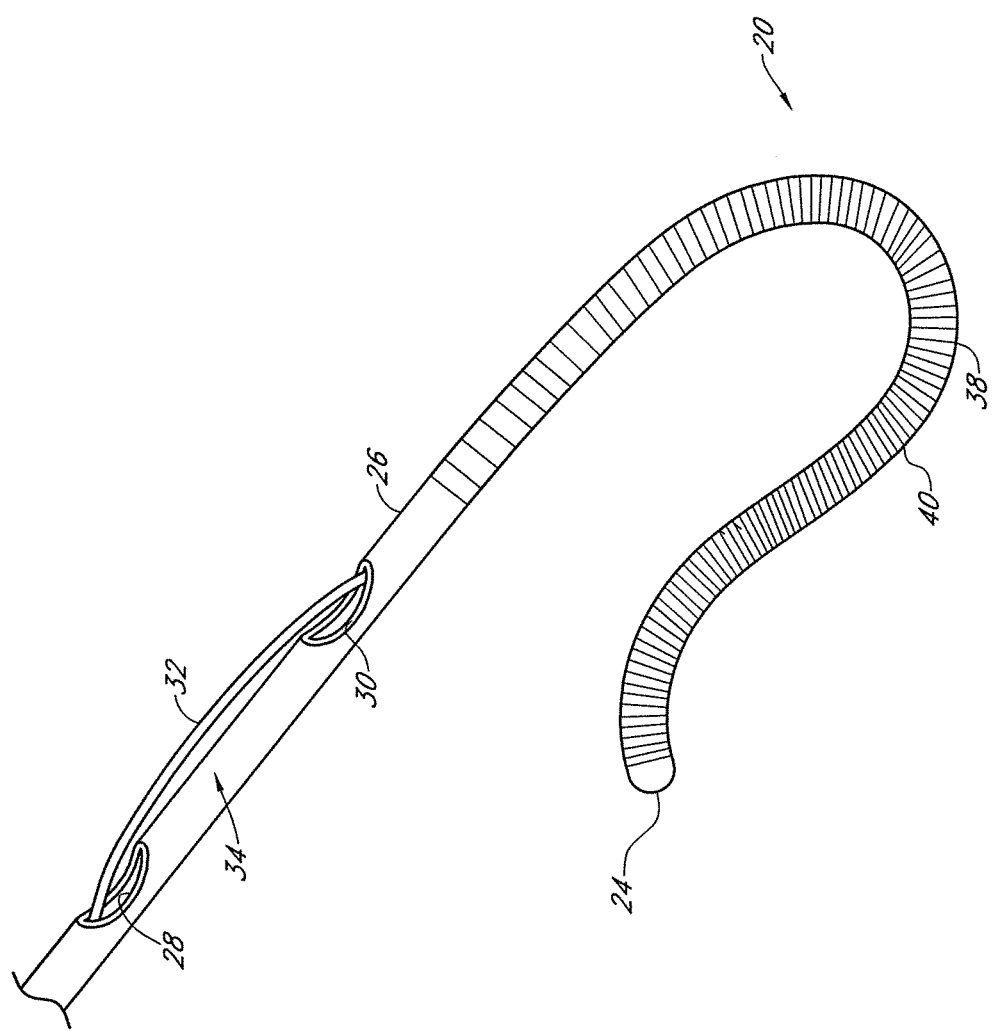

FIGS. 2A and 2B illustrate one embodiment of a pushrod 20 configured for use in positioning a bodily implant. For simplicity, only a distal portion of the pushrod 20 is shown. With reference to FIG. 2A, the pushrod 20 is tubular, including a lumen 22. A distal tip 24 of the pushrod 20 is closed, and is preferably rounded and smooth to reduce the likelihood of the tip 24 damaging the inner wall of a HAS. A sidewall 26 of the pushrod 20 includes first and second longitudinally spaced openings 28, 30. A wire 32 extends through the lumen 22 from the proximal end of the pushrod 20. The wire 32 extends outward through the first, proximal, opening 28, and back into the lumen 22 through the second, distal, opening 30. The wire 32 may be held in place by friction between the wire 32 and the edges of the openings 28, 30 where the wire 32 contacts. Alternatively, or in addition, a distal tip (not shown) of the wire 32 may be secured to an internal portion of the pushrod 20.

A space 34 bounded by the wire 32 and the sidewall 26 of the pushrod 20 forms an implant receiving space 34, as described further below. The pushrod 20 may comprise, for example, stainless steel, titanium, or any other biocompatible material having sufficient column strength but also sufficient flexibility to enable it to be advanced through a body, such as through tortuous vasculature, from an access site to a treatment site. The wire 32 may similarly comprise, for example, stainless steel, titanium, or any other biocompatible material.

An implant 36, which may be similar to the fibrous implant 10 shown in FIG. 1A, is held in the space 34 between the wire 32 and the sidewall 26 of the pushrod 20 so that the pushrod 20 can be used to advance the implant 36 through the body to the treatment site. For example, the treatment site may be in a hollow anatomical structure (HAS), such as a vessel. When the implant 36 is positioned as desired at the treatment site, the operator applies a proximally directed pulling force on the wire 32 so that the wire 32 is withdrawn from the openings 28, 30 in the pushrod 20. Withdrawing the wire 32 releases the implant 36 from the space 34 between the wire 32 and the sidewall of the pushrod 20. The pushrod 20 is subsequently withdrawn, leaving the implant 36 at the treatment site.

With further reference to FIG. 2A, a distal portion 38 of the pushrod 20 includes a spiral-shaped cut 40 through the sidewall 26. The spiral cut 40 may, for example, be formed with a laser, or via any other suitable method. With reference to FIG. 2B, the spiral cut 40 augments the flexibility of the distal portion 38, and renders the distal tip 24 of the pushrod 20 atraumatic so that it does not damage inner walls of HASs, even when advanced through HASs without a sheath. In the illustrated embodiment, the spiral cut 40 decreases in pitch in the proximal-to-distal direction along the length of the pushrod 20. However, in alternative embodiments the pitch of the spiral cut 40 may remain constant along the length of the pushrod 20.

Advantageously, the pushrod 20 illustrated in FIGS. 2A-2B is operable to position the implant 36 within a HAS without a need for a sheath to extend all the way to the distal end of the treatment site, due to the presence of the atraumatic tip 24. A standard sheath (e.g., 7-8 Fr, 7-11 cm, for SSV or GSV) can be used to insert the pushrod-implant assembly into the vein, and the pushrod-implant assembly can be advanced distally beyond the distal end of the sheath to the distal end of the treatment site. Once the pushrod 20 and implant 36 are fully distal in the vein, the introducer sheath can be pulled back proximally over the pushrod 20 and removed.

In some cases, natural radial expansion of the implant may not be sufficient to properly occlude the HAS, and it may be desirable to further expand the implant, while providing a greater density of material in the treatment area. Further, initial placement of a bodily implant may not be as desired. In such cases, it is desirable to reposition the implant one or more times until the desired placement is achieved. The present embodiments provide apparatus and methods for positioning and compacting a bodily implant. For example, the implant includes at least a distal pull string for compacting at least a portion of a distal portion of the implant, and a proximal pull string for compacting at least a portion of a proximal portion of the implant. Some embodiments may further include at least an intermediate pull string for compacting at least a portion of an intermediate portion of the implant. Methods for compacting the implant comprise pulling the distal pull string and subsequently pulling the proximal pull string to compact the implant in the distal-to-proximal direction (i.e., distal portion first, then proximal portion). By compacting the implant in this manner, the implant may radially expand further than the implant would naturally. Further, compacting the implant in the distal-to-proximal direction also facilitates the ability to reverse the compaction operation so that the implant can be repositioned within the body in the event that the initial placement is not as desired.

Figure 3:
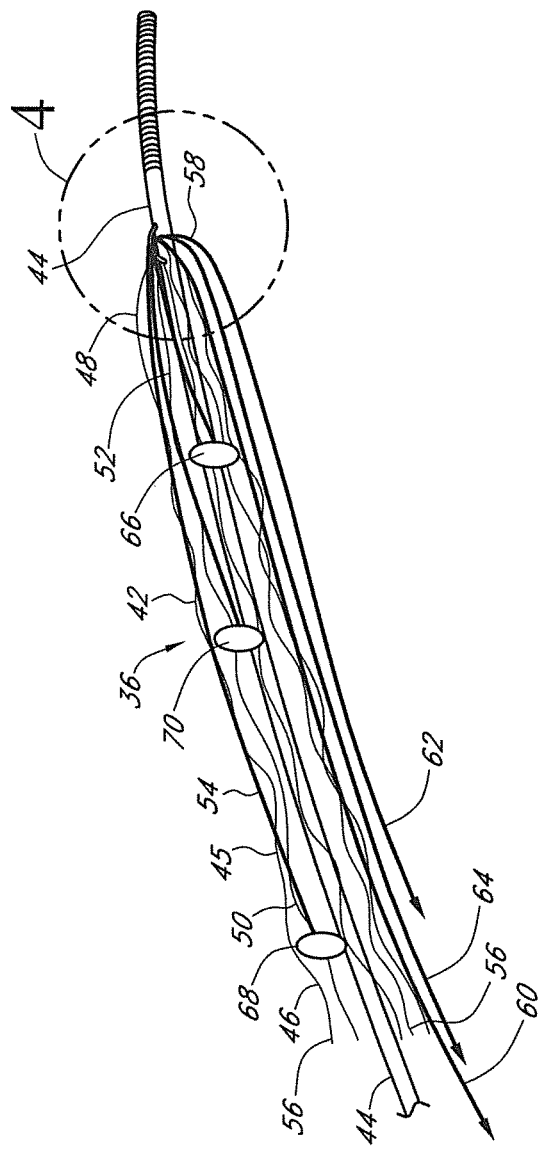
FIG. 3 is a side elevation view of a fibrous bodily implant and a pushrod configured for positioning the implant, according to the present embodiments.

FIG. 3 illustrates one embodiment of the present fibrous bodily implant 42. The implant 42 is shown in combination with a pushrod 44, which is configured for use in a method of positioning and compacting the implant 42, as described in detail below. The implant 42 comprises a plurality of fibers 45, the properties of which may be similar to that described above with respect to the implant 10 of FIG. 1A. The implant 42 further comprises at least a proximal end 46 and a distal end 48, and a proximal portion 50 adjacent the proximal end 46, a distal portion 52 adjacent the distal end 48, and an intermediate portion 54 between the proximal portion 50 and the distal portion 52.

Each of the fibers 45 includes opposite end portions 56 and a mid-portion 58. When the implant 42 is secured to the pushrod 44 as illustrated in FIG. 3, the end portions 56 of the fibers 45 lie adjacent the proximal end 46 of the implant 42, and the mid-portion 58 lies adjacent the distal end 48 of the implant 42. As described in more detail below, the mid-portions 58 of the fibers 45, which correspond to the distal end 48 of the implant 42, are secured to the pushrod 44, and the fibers 45 extend proximally along the pushrod 44 from the point of attachment.

The implant 42 further comprises a plurality of pull strings 60, 62, 64, which are configured for compacting the implant 42, as described in detail below. The illustrated embodiment comprises three pull strings 60, 62, 64, including a distal pull string 60, a proximal pull string 62, and an intermediate pull string 64. However, in alternative embodiments any number of pull strings may be provided, including one, two, or more than three. For example, only the distal pull string 60 and proximal pull string 62 may be present. The pull strings 60, 62, 64 may comprise the same material(s) as the fibers 45 of the implant 42, such as PGA and/or PLA, or any other material. However, the material(s) of the pull strings 60, 62, 64 is preferably bioabsorbable or bioresorbable.

The distal pull string 60 includes a first end 66 that is secured to the implant 42 in the distal portion 52. Similarly, the proximal pull string 62 includes a first end 68 that is secured to the implant 42 in the proximal portion 50, and the intermediate pull string 64 includes a first end 70 that is secured to the implant 42 in the intermediate portion 54. In certain embodiments, the pull strings 60, 62, 64 may be secured to the implant 42 by tying. However, any suitable attachment method is contemplated, such as fusing the materials (e.g., by heat or chemical melting) or adhesively bonding. When the implant 42 is secured to the pushrod 44 as illustrated in FIG. 3, each of the pull strings 60, 62, 64 extends distally along the implant 42 and pushrod 44 from each pull string's 60, 62, 64 respective first end 66, 68, 70, loops around the point of attachment of the implant 42 to the pushrod 44, and extends proximally along the implant 42 and pushrod 44 from the point of attachment to the pushrod 44.

Figure 4:
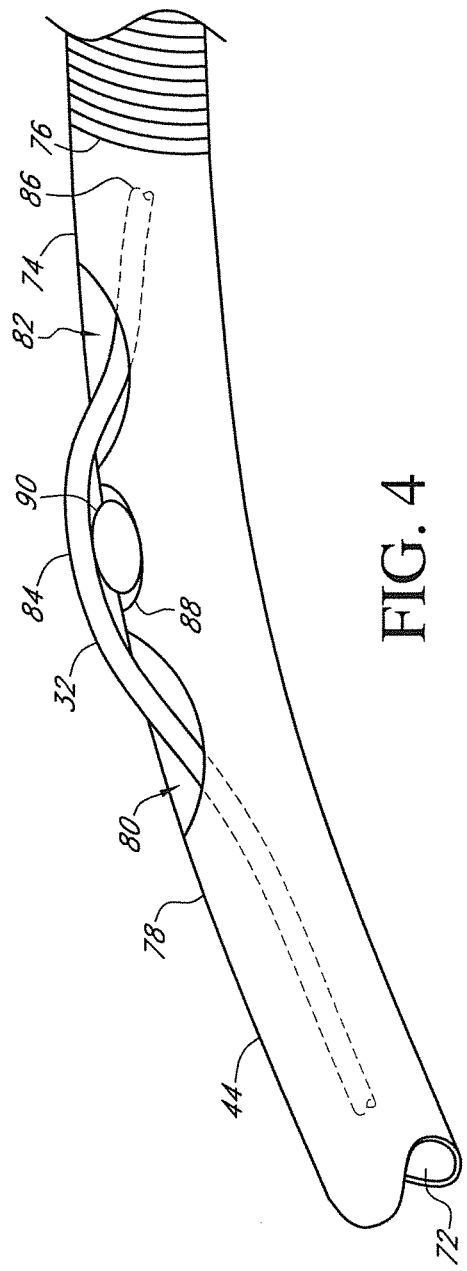
FIG. 4 is a detail view of the portion of FIG. 3 indicated by the circle 4-4 in FIG. 3.

FIG. 4 is a detail view of the implant 42 and the pushrod 44 in the area where the implant 42 is secured to the pushrod 44, as indicated by the circle 4-4 in FIG. 3. For simplicity, FIG. 4 shows the pushrod 44 in isolation, but the configuration of the implant 42 relative to the pushrod 44 is described below with further reference to FIGS. 4 and 5.

With reference to FIG. 4, the pushrod 44 is tubular and defines a lumen 72. A distal portion 74 of the pushrod 44 may include a spiral cut 76 to enhance the flexibility of the pushrod 44 in the distal portion 74, as described above with respect to the pushrod 20 of FIG. 2. However, in alternative embodiments the spiral cut 76 may be omitted.

As shown in FIG. 4, a sidewall 78 of the pushrod 44 defines a first opening 80 and a second opening 82 in the distal portion 74. The first and second openings 80, 82 are spaced from one another along a longitudinal axis of the pushrod 44. The lumen 72 of the pushrod 44 receives an elongate flexible wire 32. A distal portion 84 of the wire 32 extends outward through the first opening 80 in the pushrod 44, and back into the lumen 72 through the second opening 82 in the pushrod 44. A distal tip 86 of the wire 32 resides adjacent the distal portion 74 of the pushrod 44 inside the lumen 72. The wire 32 is held in place by friction at the points of contact between the wire 32 and the edges of the first and second openings 80, 82. The wire 32 comprises any suitable flexible and biocompatible material, such as stainless steel or titanium.

Figure 5:
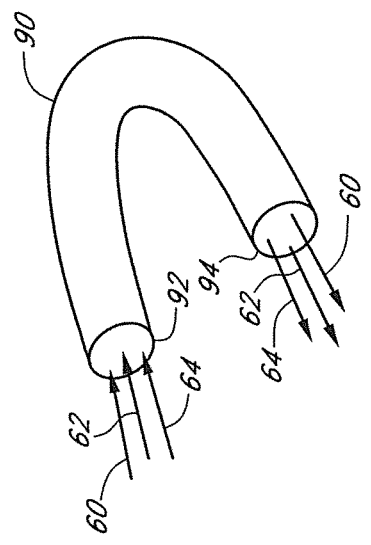
FIG. 5 is a side perspective view of a guide member for use with the implant and the pushrod of FIGS. 3 and 4.

The sidewall 78 of the pushrod 44 may further define a third opening 88 located between the first and second openings 80, 82. With reference to FIGS. 4 and 5, a guide member 90 may seat within a depression formed in the sidewall 78 by the third opening 88. With reference to FIG. 4, when the tubular pushrod 44 is viewed in profile, the third opening 88 appears as a U-shaped depression. The guide member 90 may extend transversely across the pushrod 44 and seats within the third opening 88 with the wire 32 overlying the guide member 90. Alternatively, the third opening 88 may not be present, and the guide member 90 may sit directly against the sidewall 78.

With reference to FIG. 5, the guide member 90 is tubular and U-shaped. The pull strings 60, 62, 64 of the implant 42 extend through the guide member 90, entering at a first end 92 of the guide member 90 and exiting at a second end 94 of the guide member 90. The guide member 90, which is held in place between the wire 32 and the third opening 88, or alternatively against the sidewall 78, thus couples the pull strings 60, 62, 64 to the pushrod 44. The guide member 90 provides a smooth, low-friction internal surface for each of the pull strings 60, 62, 64 to bear against as each is pulled to compact the implant 42, as described below. However, in still other alternative embodiments, the guide member 90 may be omitted such that the pull strings 60, 62, 64 are held in the space between the wire 32 and the pushrod 44 without the intervening guide member 90.

The guide member 90 is preferably constructed of one or more implantable materials, such as one or more bioabsorbable or bioresorbable materials, so that the guide member 90 is implantable within the body along with the implant 42. The guide member 90 may be constructed of the same material as the implant 42, or a different material. For example, the guide member 90 may comprise PGA and/or PLA, or any other suitable bioabsorbable or bioresorbable material.

Figure 6:
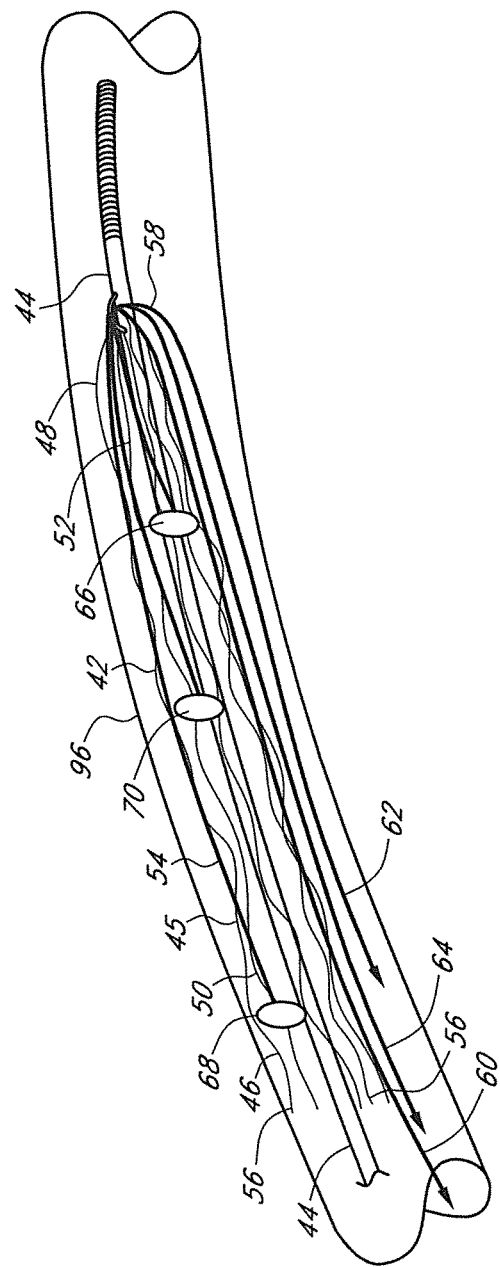
FIGS. 6-9 are side elevation views of the implant and pushrod of FIG. 3 as shown in connection with a method for placing and compacting the implant, according to the present embodiments, illustrating various stages of implant compaction.
Figure 7:
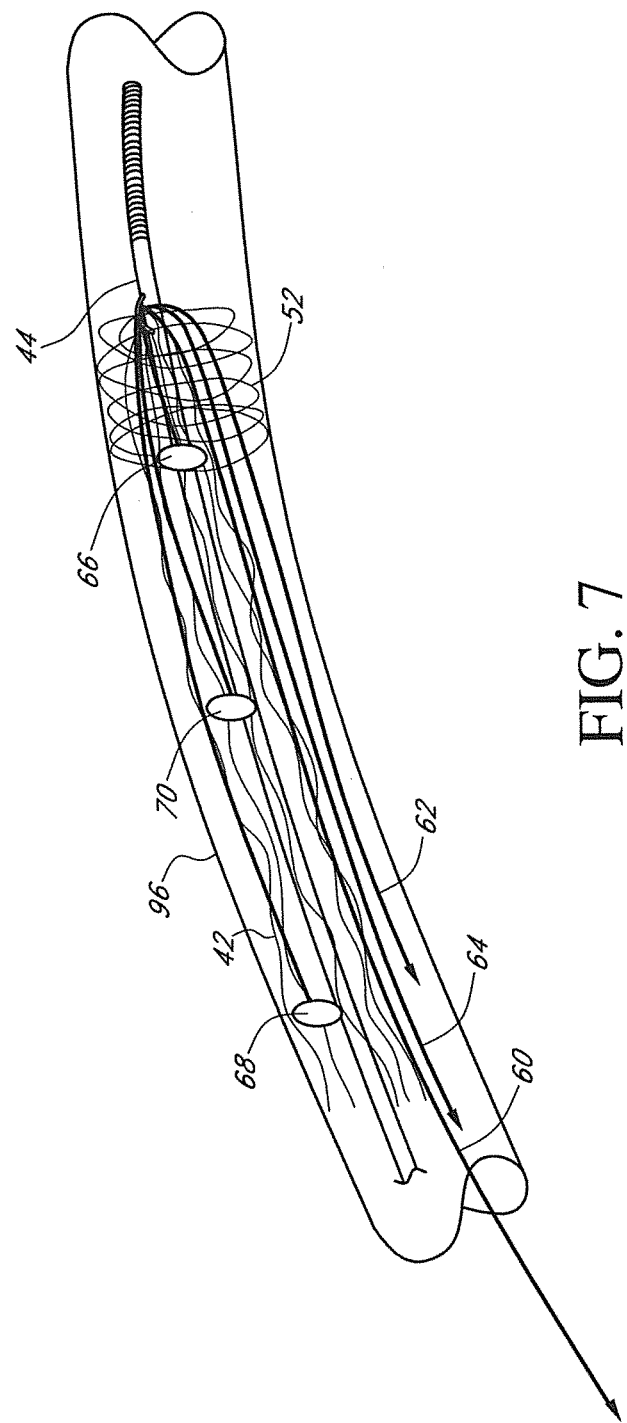

FIG. 6 illustrates the implant 42 and pushrod 44 of FIG. 3 positioned within a HAS 96 at a treatment site. When the implant 42 is positioned as desired, it may be compacted by pulling the three pull strings 60, 62, 64 in distal to proximal succession. For example, with reference to FIG. 7, first the operator pulls the distal pull string 60 by applying a proximally directed pulling force on a portion of the distal pull string 60 that extends outwardly of the access site. Because the distal pull string 60 extends through the U-shaped guide member 90, the proximally directed pulling force is translated into a distally directed pulling force applied to the implant 42 at the point where the first end 66 of the distal pull string 60 is attached to the implant 42. The implant 42 thus compacts under the influence of the force applied to it by the distal pull string 60. However, because the distal pull string 60 is attached to the distal portion 52 of the implant 42 in the distal portion 52 thereof, only the distal portion 52 of the implant 42 compacts during this phase of compaction, as shown in FIG. 7. Specifically, only that portion of the implant 42 distal to the point where the first end 66 of the distal pull string 60 attaches to the implant 42 compacts. Although, the intermediate portion 54 and proximal portion 50 of the implant 42 may move distally without compacting.

Figure 8:
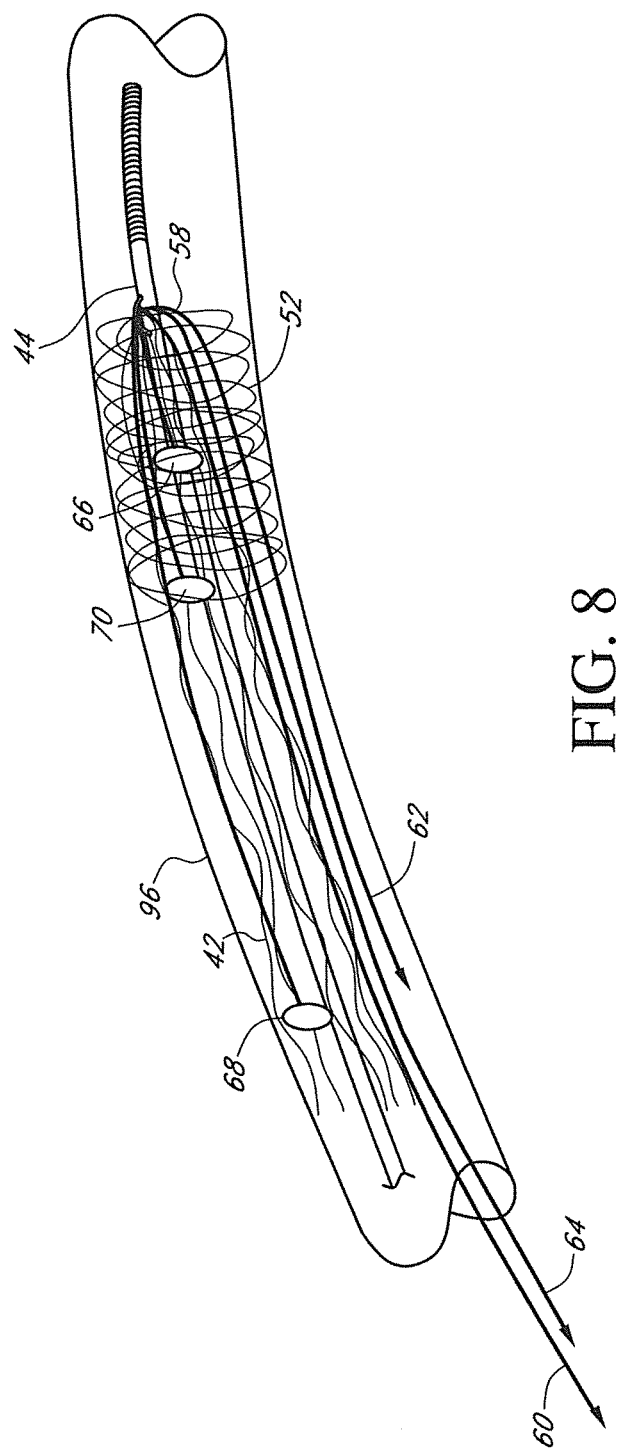

With reference to FIG. 8, after the distal portion 52 of the implant 42 has been compacted as desired, the operator next pulls the intermediate pull string 64 by applying a proximally directed pulling force on a portion of the intermediate pull string 64 that extends outwardly of the access site. Because the intermediate pull string 64 extends through the U-shaped guide member 90, the proximally directed pulling force is translated into a distally directed pulling force applied to the implant 42 at the point where the first end 70 of the intermediate pull string 64 is attached to the implant 42. The implant 42 thus compacts under the influence of the force applied to it by the intermediate pull string 64. However, because the intermediate pull string 64 is attached to the implant 42 in the intermediate portion 54 thereof, only the intermediate portion 54 of the implant 42 compacts during this phase of compaction, as shown in FIG. 8. Specifically, only that portion of the implant 42 distal to the point where the first end 70 of the intermediate pull string 64 attaches to the implant 42 compacts.

Figure 9:
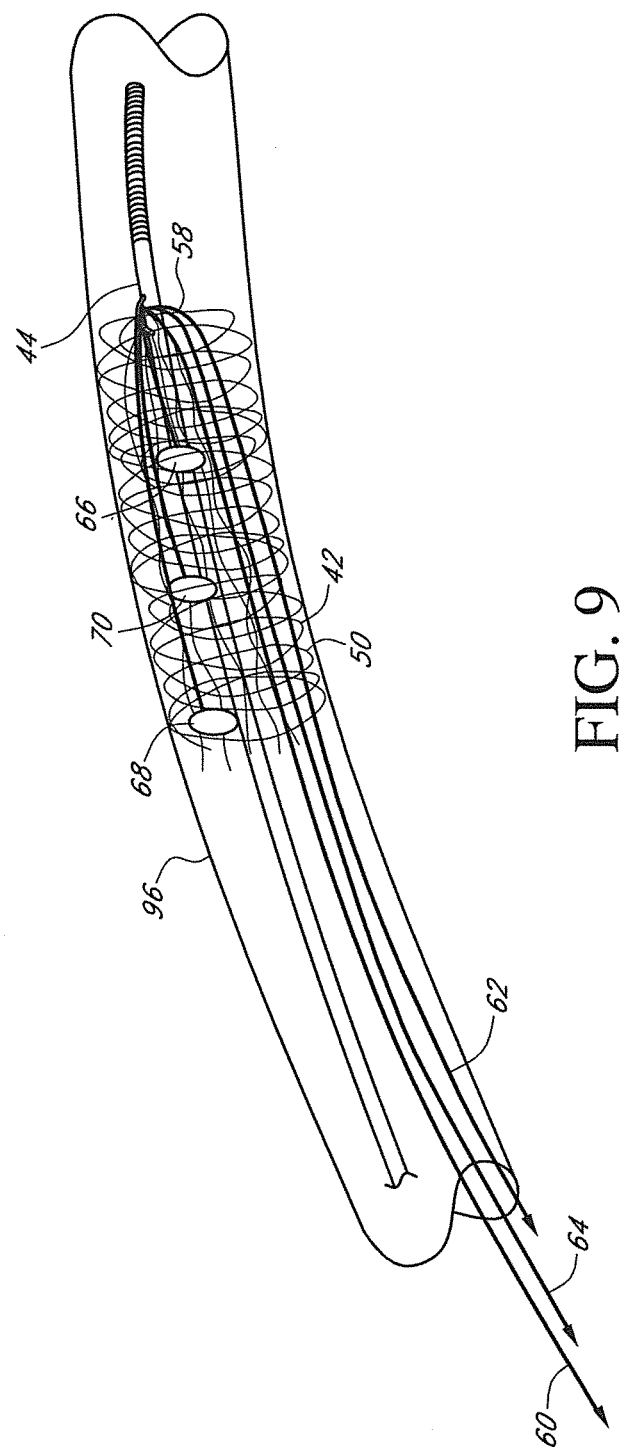

With reference to FIG. 9, after the intermediate portion 54 of the implant 42 has been compacted as desired, the operator next pulls the proximal pull string 62 by applying a proximally directed pulling force on a portion of the proximal pull string 62 that extends outwardly of the access site. Because the proximal pull string 62 extends through the U-shaped guide member 90, the proximally directed pulling force is translated into a distally directed pulling force applied to the implant 42 at the point where the first end 68 of the proximal pull string 62 is attached to the implant 42. The implant 42 thus compacts under the influence of the force applied to it by the proximal pull string 62. However, because the proximal pull string 62 is attached to the implant 42 in the proximal portion 50 thereof, only the proximal portion 50 of the implant 42 compacts during this phase of compaction, as shown in FIG. 9. Specifically, only that portion of the implant 42 distal to the point where the first end 68 of the proximal pull string 62 attaches to the implant 42 compacts.

After the implant 42 has been fully compacted, and the implant 42 is positioned as desired, the operator applies a proximally directed pulling force to the wire 32. The distal tip 86 of the wire 32 withdraws from the openings 80, 82 (FIG. 4) in the sidewall 78 of the pushrod 44, thus releasing the implant 42 from the pushrod 44. The pushrod 44 is then withdrawn from the HAS 96, leaving the compacted implant 42 in place at the treatment site. Prior to withdrawing the pushrod 44, the wire 32 may be further withdrawn with respect to the pushrod 44 until it is fully withdrawn from the lumen 72 of the pushrod 44. Alternatively, the wire 32 may be left partially disposed within the pushrod 44, and the pushrod 44 and the wire 32 may be withdrawn together from the HAS 96.

Compacting the implant 42 causes the implant 42 to shorten in the longitudinal direction, to expand in the radial direction, and to increase in density at the treatment site, as shown in FIGS. 6-9. Preferably, the radial expansion and density increase is sufficient to cause the implant 42 to completely occlude the HAS 96. The implant 42 preferably forms a scaffold for occlusive ingrowth and clotting in the implant 42, eventually forming a durable occlusion of the HAS.

Compacting the implant 42 in the distal-to-proximal direction advantageously aids in repositioning the implant 42. For example, if the initial placement of the implant 42 at the treatment site is not as desired, but the implant 42 has already been partially or fully compacted, the compaction steps can be reversed by advancing the pushrod 44 farther into the HAS 96. The implant 42, which is still fixed to the pushrod 44, will elongate in the distal-to-proximal direction as the pushrod 44 advances, because the advancing pushrod 44 applies a distally directed force to the distal end 48 of the implant 42, which couples with friction between the compacted implant 42 and the inner walls of the HAS 96 to create a tensile force on the implant 42. The tensile force lengthens the implant 42 and reverses the compaction. When the compaction has been reversed sufficiently that the implant 42 may freely move proximally and distally within the HAS 96, the operator can reposition the implant 42 as desired, as many times as desired, before again compacting the implant 42 in the same manner described above.

As discussed above, the present embodiments may include any number of pull strings. For example, in some embodiments only two pull strings are provided, where a distal pull string is secured to the distal portion of the implant and a proximal pull string is secured to the proximal portion of the implant. In such embodiments, a process for compacting the implant includes first pulling the distal pull string to compact the implant distal portion, then pulling the proximal pull string to compact the implant proximal portion. In embodiments including more than three pull strings, the pull strings may be pulled successively to compact the implant in phases, where the compaction phases proceed in the distal-to-proximal direction.

Figure 10:
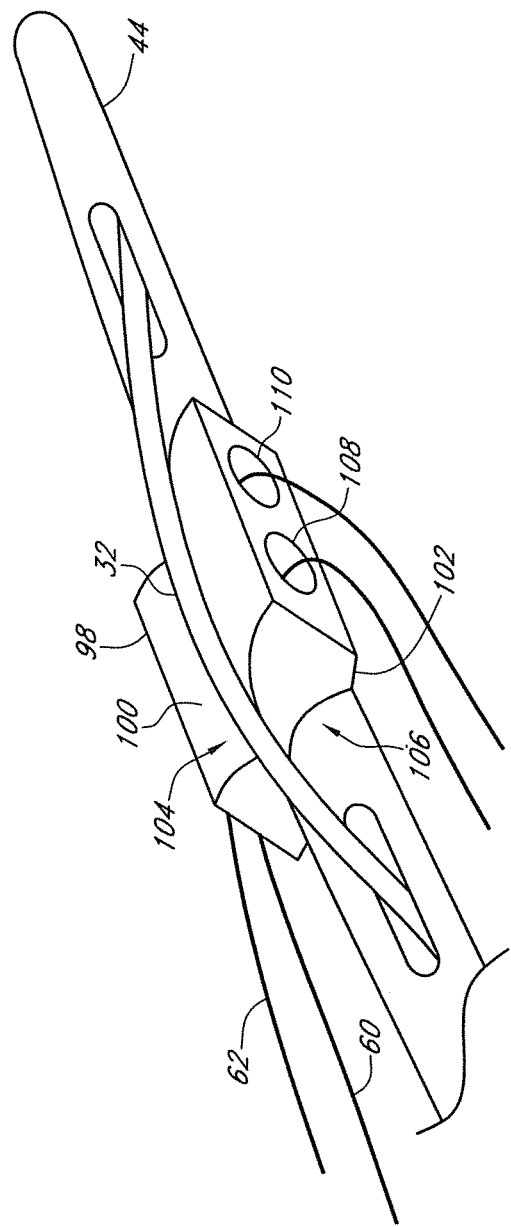
FIG. 10 is a side perspective view of another embodiment of a system and method for placing and compacting a fibrous bodily implant.

FIG. 10 illustrates an alternative embodiment of a guide member 98. The guide member 98 includes upper and lower surfaces 100, 102 defining central concave channels 104, 106 that receive the wire 32 and the pushrod 44, respectively. Engagement of the wire 32 and the pushrod 44 with their respective channels 104, 106 augments the stability of the guide member 98 within the space defined between the wire 32 and the pushrod 44. First and second U-shaped passages 108, 110 extend through the guide member 98 to receive the pull strings 60, 62. In the illustrated embodiment, only the distal and proximal pull strings 60, 62 are shown for convenience. The provision of multiple passages 108, 110 enables the pull strings 60, 62 to be isolated from one another, which reduces friction when pulling the pull strings 60, 62 to compress the implant 42. In alternative embodiments, any number of passages may be provided, such as a separate passage for each pull string.

It is to be understood that the foregoing description is intended to illustrate and not limit the scope of the invention, which is defined by the scope of the appended claims. Other embodiments are within the scope of the following claims.

What is claimed is:

1. A medical treatment system, comprising:
    an elongate, flexible, tubular pushrod, the pushrod having a distal end;
    a guide member coupled adjacent the distal end of the pushrod;
    an implant coupled adjacent the distal end of the pushrod and proximal of the guide member and extending proximally along the pushrod, the implant having a proximal portion adjacent a proximal end and a distal portion adjacent a distal end, the implant comprising a plurality of bioabsorbable fibers;
    a distal pull string extending through the guide member and secured to the implant at a first attachment point within the distal portion of the implant; and
    a proximal pull string extending through the guide member and secured to the implant at a second attachment point within the proximal portion of the implant,
    wherein pulling the distal string in a proximal direction compacts at least a portion of the distal portion of the implant in a distal direction and pulling the proximal pull string in a proximal direction compacts at least a portion of the proximal portion of the implant in a distal direction.

2. The system of claim 1, wherein the implant further comprises an intermediate portion disposed between the distal portion and the proximal portion, and an intermediate pull string extending through the guide member and secured to the implant at a third attachment point within the intermediate portion of the implant, wherein pulling the intermediate pull string in a proximal direction compacts at least a portion of the intermediate portion of the implant in a distal direction.

3. The system of claim 1, wherein the guide member is bioabsorbable.

4. The system of claim 1, wherein the guide member is tubular and U-shaped.

5. The system of claim 1, further comprising an elongate, flexible wire extending through the pushrod.

6. The system of claim 5, wherein a sidewall of the tubular pushrod defines a first opening and a second opening adjacent the distal end of the pushrod.

7. The system of claim 6, wherein the first and second openings in the pushrod are spaced from one another axially along a length of the pushrod.

8. The system of claim 7, wherein the wire extends out of the pushrod through the first opening and extends back into the pushrod through the second opening.

9. The system of claim 8, wherein the guide member extends through a space bounded by the pushrod and the wire and located between the first and second openings in the pushrod.

10. The system of claim 8, wherein the implant extends through a space bounded by the pushrod and the wire and located between the first and second openings in the pushrod.

11. The system of claim 1, wherein the guide member defines at least first and second internal passages extending therethrough.

12. A medical treatment system, comprising:
    an elongate, flexible pushrod having a distal end;
    an implant coupled adjacent the distal end of the pushrod and extending proximally along the pushrod, the implant having a proximal portion adjacent a proximal end and a distal portion adjacent a distal end, the implant comprising a plurality of bioabsorbable fibers;
    a distal pull string secured to the implant at a first attachment point within the distal portion of the implant, the distal pull string extending distally along the pushrod from the first attachment point to where the implant is coupled adjacent the distal end of the pushrod and then extending proximally along the implant; and
    a proximal pull string secured to the implant at a second attachment point within the proximal portion of the implant, the proximal pull string extending distally along the pushrod from the second attachment point to where the implant is coupled adjacent the distal end of the pushrod and then extending proximally along the implant.

13. The system of claim 12, wherein the pushrod comprises a hypotube.

14. The system of claim 13, wherein a side wall of the distal end of the pushrod includes a spiral-shaped cut.

15. The system of claim 12, further comprising a guide member coupled adjacent the distal end of the pushrod and distal to the distal end of the implant.

16. The system of claim 15, wherein the pull strings extend through the guide member.

17. The system of claim 15, wherein the guide member is bioabsorbable.

18. The system of claim 15, wherein the guide member is tubular and U-shaped.

19. The system of claim 15, wherein the guide member defines first and second internal passages extending therethrough.

20. The system of claim 12, further comprising an elongate, flexible wire extending through the pushrod.

21. The system of claim 20, wherein a sidewall of the pushrod defines a first opening and a second opening adjacent the distal end of the pushrod.

22. The system of claim 21, wherein the first and second openings in the pushrod are spaced from one another axially along a length of the pushrod.

23. The system of claim 22, wherein the wire extends out of the pushrod through the first opening and extends back into the pushrod through the second opening.

24. The system of claim 23, further comprising a guide member, wherein the guide member extends through a space bounded by the pushrod and the wire and located between the first and second openings in the pushrod.

25. The system of claim 23, wherein the distal pull string and the proximal pull string extend through a space bounded by the pushrod and the wire and located between the first and second openings in the pushrod.

26. A medical treatment system, comprising:
    an elongate, flexible, tubular pushrod, the pushrod having a distal end;
    an elongate, flexible wire extending through the pushrod, wherein a sidewall of the tubular pushrod defines a first opening and a second opening adjacent the distal end of the pushrod and the wire extends out of the pushrod through the first opening and extends back into the pushrod through the second opening, thereby defining a space bounded by the pushrod and the wire between the first and second openings in the pushrod;

an implant coupled adjacent the distal end of the pushrod via the space bounded by the pushrod and the wire and extending proximally along the pushrod, the implant having a proximal portion adjacent a proximal end, and a distal portion adjacent a distal end, the implant comprising a plurality of bioabsorbable fibers;

a distal pull string extending through the space bounded by the pushrod and the wire, and secured to the implant at a first attachment point within the distal portion of the implant; and a proximal pull string extending through the space bounded by the pushrod and the wire, and secured to the implant at a second attachment point within the proximal portion of the implant, wherein pulling the distal string in a proximal direction compacts at least a portion of the distal portion of the implant in a distal direction, and pulling the proximal pull string in a proximal direction compacts at least a portion of the proximal portion of the implant in a distal direction.

* * * * *